United States Patent [19]

Naumann et al.

[11] Patent Number: 4,922,041

[45] Date of Patent: May 1, 1990

[54] METHOD FOR PRODUCING CF$_3$I

[75] Inventors: Dieter Naumann, Dortmund; Wieland Tyrra, Herne; Birgit Kock, Münster; Werner Rudolph, Hannover; Bernd Wilkes, Laatzen, all of Fed. Rep. of Germany

[73] Assignee: Kali-Chemie AG, Hannover, Fed. Rep. of Germany

[21] Appl. No.: 195,797

[22] Filed: May 19, 1988

[30] Foreign Application Priority Data

May 22, 1987 [DE] Fed. Rep. of Germany ....... 3717358

[51] Int. Cl.$^5$ ...................... C07C 17/20; C07C 17/22
[52] U.S. Cl. .................................... 570/141; 570/140; 570/142
[58] Field of Search ............... 570/137, 141, 142, 163, 570/140

[56] References Cited

U.S. PATENT DOCUMENTS 4,701,569 10/1987 Francese et al.

OTHER PUBLICATIONS

Pummer and Wall, J. Research NBS, 63A, 167, (1959).
Banks et al., J. Chem. Soc., "The Reaction of Bromine Trifluoride and Iodine, Pentafluoride . . . ", pp. 2188–2190, (1949).
Henne et al., J. Am. Chem. Soc., "The Degradation of Silver Trifluoroacetate . . . ", 72 pages, 3806–3807, (1950).
Emeleus et al., J. Chem. Soc., "Organometallic Fluorine Compounds", pp. 2953–2956, (1949).
Habeeb et al., J. Org. Chem. 195, "The Electrochemical Synthesis of Neutral and Anionic . . . ", pp. 117–127, (1980).
Hazeldine, J. Chem. Soc., pp. 1273–1275, 1954.
McBee et al., J. Org. Chem., vol. 28, pp. 1131–1132, 1963.
Blancou et al., J.C.S. Chem. Comm., pp. 885–886, 1976.
Burton et al., J. Am. Chem. Soc., vol. 107, pp. 5014–5015, 1985.

Primary Examiner—John Doll
Assistant Examiner—Stuart L. Hendrickson
Attorney, Agent, or Firm—Foley & Lardner, Schwartz, Jeffery, Schwaab, Mack, Blumenthal & Evans

[57] ABSTRACT

A method for producing trifluoroiodomethane in which a metal Mt selected from the group magnesium, zinc, cadmium, bismuth and tin is reacted in a first step (a) with a trifluorohalomethane, and the resulting reaction mixture is further reacted in a second step (b) with a component containing iodine to produce CF$_3$I. Compounds corresponding to the formula CF$_3$.Zn.X.nL are also described.

17 Claims, No Drawings

METHOD FOR PRODUCING CF$_3$I

BACKGROUND OF THE INVENTION

The present invention relates to a method for producing trifluoroiodomethane and to compounds of the general Formula CF$_3$.Zn.X.nL.

Trifluoroiodomethane may be used, for example, as a trifluoromethylation reagent suitable for the preparation of pharmaceuticals or herbicides, as a plasma etching gas, or for preparing trifluoronitrosomethane which may be copolymerized with tetrafluoroethylene to form a non-flammable rubber.

Several methods for preparing CF$_3$I are known. According to Banks et al., *J. Chem. Soc.* (1948), pages 2188–2190, CF$_3$I is isolated—as well as CF$_3$H—as a reaction product from the reaction, described as violent, of CI$_4$ with IF$_5$. A further possibility for preparing CF$_3$I is by thermal decomposition of CF$_3$COOAg in the presence of iodine (A. L. Henne, W. G. Finnegan, *J. Am. Chem. Soc.* 72, (1950), pages 3806–3807). However, this reaction easily gets out of control. In addition, the possibility of preparing trifluoroiodomethane by cleaving CF$_3$HgI or (CF$_3$)$_2$Hg with iodine is known (H. J. Emeleus, R. N. Haszeldine, *J. Chem. Soc.* (1949), pages 2953–2956). Both mercury compounds are characterized by high toxicity and in addition are produced from CF$_3$I and mercury. (CF$_3$)$_2$Hg can indeed also be prepared by decarboxylation of (CF$_3$COO)$_2$Hg, but this compound is also highly toxic and its use is undesirable for environmental protection reasons.

The heretofore known methods for preparing CF$_3$I have the disadvantages that they require reaction conditions which are difficult to control, require CF$_3$I as a starting product and are thus economically disadvantageous and/or involve ecological problems.

SUMMARY OF THE INVENTION

It is the object of the present invention to remedy the foregoing disadvantages by providing an economical and at the same time ecologically acceptable method for producing CF$_3$I.

This and other objects of the invention are achieved by providing a method for producing CF$_3$I comprising the steps of:

(a) reacting CF$_3$X, wherein X represents halogen, particularly chlorine or bromine, with a metal Mt from the group magnesium, zinc, cadmium, bismuth and tin, preferably in a solvent; and (b) reacting the resulting reaction mixture with a compound I-Y, wherein Y represents either iodine or a ligand which is more electronegative than iodine, to produce CF$_3$I.

In a preferred manner of carrying out the method of the invention, the metal zinc is used in step (a).

A modification of the method for producing CF$_3$I is characterized by:

(a) reacting CF$_3$X, wherein X has the meaning given above, with zinc, preferably in a solvent, wherein a complexing agent L is added to the reaction mixture before, during or after the reaction;

(a1) isolating the resulting organometallic compound corresponding to the Formula (I)

$$CF_3.Zn.X.nL \quad (I)$$

wherein n is the number 1 or 2 and L represents the complexing agent L;

(b) reacting the compound of Formula (I) isolated in step (a1) with a compound I-Y, wherein Y has the meaning given above, to produce CF$_3$I.

The zinc compounds of Formula (I) are novel and are likewise part of the invention.

DETAILED DESCRIPTION OF THE PREFERRED EMBODIMENTS

In the compounds of Formula (I), X represents halogen, preferably chlorine or bromine; n represents the number 1 or 2, and L represents a complexing agent L.

The complexing agent L may be a mono- or multi-dentate complexing compound and inorganic or organic in nature. Preferably L is an organic compound. It is particularly preferred that L be an organic, polar, aprotic complexing agent. Compounds selected from the group consisting of cyclic or acyclic ethers, optionally substituted carboxylic acid amides, optionally substituted lactams, nitriles, sulfoxides, amines and/or pyridines are well suited for use as the complexing agent L. For instance, tetrahydrofuran, diethyl ether, N,N-dimethylformamide, N,N-dimethylacetamide, N-methyl pyrrolidone, N-ethyl pyrrolidone, acetonitrile, benzonitrile, triethylamine, dimethyl sulfoxide, pyridine, substituted pyridine such as methyl pyridine, can be mentioned as possible complexing agents. Multi-dentate complexing agents are less preferred, but may also be used. Among the large number of multi-dentate ligands known to persons skilled in the art, dioxane, ethylene glycol methyl ether, optionally substituted diamines and dipyridyl may be specifically mentioned as suitable.

Preferably, L is an N-disubstituted carboxylic acid amide, particularly N,N-dimethylformamide (DMF).

In the compounds of Formula (I), n preferably has the meaning 2. The compound CF$_3$.Zn.Br.2DMF is especially preferred.

The compounds of formula (I) may be produced by reacting CF$_3$X with zinc, preferably in a solvent, whereby a complexing agent L is added to the reaction mixture before, during or after the reaction, and the resulting organometallic compound having the Formula (I) is isolated. Preferably work is carried out under the exclusion of moisture and oxygen. This can be achieved by using inert gas atmospheres (protective gases), e.g. nitrogen. The isolation of the compounds of Formula (I) takes place according to methods which are known to persons skilled in the art, for instance by removing the solvent or by crystallization. If work has been carried out under elevated pressure, it is advantageous to first relieve the pressure to normal pressure. In addition, it may be advantageous to free the reaction mixture of unreacted zinc—e.g. by filtering or decanting. The temperature of the reaction mixture during isolation of the compounds should not exceed approximately 60° C., preferably approximately 50° C. The removal of solvents can be promoted by applying reduced pressure. The compounds of Formula (I) remain as crystalline solid residues. They may be freed from any adhering solvent residues by washing, for instance with CCl$_3$F or toluene. In order to avoid decomposition reactions, the compounds are stored and further processed under a protective gas atmosphere, e.g. nitrogen.

The compounds of Formula (I) can be used, for example, as intermediates in producing CF$_3$I.

The reaction in step (a) and/or in step (b) can be carried out in a solvent. Polar aprotic solvents or solvent mixtures are considered preferred solvents. They are preferably selected from the group consisting of cyclic or acyclic ethers, optionally substituted carboxylic acid amides, optionally substituted lactams, nitriles, sulfoxides, amines and/or pyridines. Tetrahydrofuran, dioxane, diethyl ether, N,N-dimethylformamide, N,N-dimethylacetamide, N-methyl pyrrolidone, N-ethyl pyrrolidone, acetonitrile, benzonitrile, triethylamine, dimethyl sulfoxide, pyridine and/or substituted pyridine such as methyl pyridine may be listed as examples.

Particularly preferred solvents are N,N-disubstituted carboxylic acid amides, particularly N,N-dimethylformamide (DMF).

If $CF_3I$ is produced in accordance with the modified process, which includes the step of isolating the compounds of Formula (I), a preferred variant is to use a solvent which is identical to the complexing agent. Preferably an N,N-disubstituted carboxylic acid amide, especially N,N-dimethylformamide, is used both as the solvent and as the complexing agent L.

The reaction in step (a) may be promoted in a known manner by the action of ultrasound, e.g. in accordance with European Patent Application No. 82,252 or European Patent Application No. 206,950.

In general, the metal, preferably in powder form, is suspended in the solvent, and the $CF_3X$ component containing the $CF_3$ group, optionally dissolved in a solvent, is added to the metal suspension at between $-60°$ C. and $+75°$ C., particularly between room temperature and $+70°$ C.

In one variant the reaction in step (a) is carried out in the presence of catalytic quantities of a metal, used in metallic and/or ionic form, which is more electropositive than the metal Mt used for the reaction in step (a). In a preferred procedure one or more metals selected from the group consisting of iron, lead and copper are used. Advantageously, salts are used which are soluble in catalytically effective amounts in the solvent which is being used. Halides, preferably iodide, or organic anions such as acetate may suitably serve as anions of the metal cation.

In a further variant, the reaction in step (a) is carried out in the presence of compounds which are known as catalysts of Grignard reactions, such as iodine or carbon tetrachloride.

In another variant, the reaction in step (a) is carried out by electrochemical oxidation of the metal, e.g. zinc, in the presence of a trifluoromethyl halide, e.g. $CF_3Br$. This may be carried out in solution and in the presence of the desired ligand or complexing agent using a zinc anode at a voltage of, for example, from about 10 to about 100 volts and a current of, for example, from about 10 to about 300 mA for a period of, for example, from about 1 to about 10 hours to produce the desired organozinc halide adduct. Such electrochemical reactions are described, for example, in J. J. Habeeb et al., *J. Organometal. Chem.* 185 (1980), page 117-127, which is hereby incorporated by reference. This variant may also be carried out particularly in combination with the above-mentioned addition of catalysts for Grignard reactions.

The reaction in step (a) may be carried out at normal pressure or at elevated pressures up to a maximum of 50 bar (absolute). Preferably the reaction is carried out at pressures between 1 bar (absolute) and the equilibrium pressure determined by the reaction temperature.

In all variants it is advantageous that the metal Mt which is used be reacted completely before the reaction in step (b) is carried out.

The reaction mixture produced in step (a) is reacted in step (b) with a compound of the Formula I-Y, which is optionally dissolved in a solvent.

When working according to the modified process, the compounds of Formula (I) isolated in step (a1) are reacted in step (b), preferably after redissolving them in a solvent, with a compound of the Formula I-Y, which is optionally dissolved in a solvent.

The reaction temperature may be in the range between $-30°$ C. and $+50°$ C., and preferably will lie at about room temperature. In the formula I-Y, Y is either iodine or a ligand which is electronegative with respect to iodine. Preferably Y represents halogen, particularly chlorine, bromine or iodine.

The trifluoroiodomethane produced in the course of the reaction can be isolated by distillation, particularly vacuum distillation.

The method of producing trifluoroiodomethane according to the invention has surprising advantages:
- the reaction in step (a) and (b) can be controlled well and thus can easily be adapted to industrial scale;
- production occurs in an ecologically acceptable manner;
- the $CF_3I$ yield is high (90% and more, relative to the ICl used as the compound of formula I-Y);
- the selectivity is high;
- the product is free of impurities.

The modified method for producing $CF_3I$, in which the compounds of Formula (I) are first isolated and then further reacted, preferably after redissolving them in a solvent, has the additional advantage that the reactants in step (b) can be used in exactly proportioned quantities. Control of the reaction through bromide determination is unnecessary with this variant.

The following examples will serve to further explain the invention, without restricting its scope.

EXAMPLE 1

CARRYING OUT OF STEP A 10 g of zinc were suspended in 200 g DMF and mixed with a catalytic 1 g amount iodine. Thereafter 10 g $CF_3Br$ were introduced at room temperature under slightly elevated pressure (1.5 bar absolute). A platinum cathode and a zinc anode were dipped into the solution and a voltage of 15 V at a current strength of 250 mA was applied. As the pressure fell, new $CF_3Br$ was introduced until all the suspended zinc was consumed. Since the zinc anode is likewise consumed, an excess of $CF_3Br$ must be used. Control of the reaction took place through bromide determinations (theoretical bromide content: 5.2%; found 4.9–5.0%).

EXAMPLE 2

CARRYING OUT OF STEP B 200 g of a DMF Grignard solution produced analagously to Example 1, which contained 15.1 wt. % $Br^- = 13.0$ wt. $CF_3^-$, was placed in a reactor at room temperature. Thereafter iodine monochloride (60 g, dissolved in 30 ml DMF) was added slowly. The resulting $CF_3I$ was distilled off during the exothermic reaction and condensed in subsequent cooling traps. $CF_3I$ yield: 92% (relative to ICl used).

EXAMPLE 3

10 g of powdered zinc were suspended in 100 ml DMF. After addition of catalytic quantities of iodine, an excess of $CF_3Br$ was dissolved at $-30°$ C. The reaction was carried out at room temperature in an ultrasound bath. Thereafter equimolar quantities of ICl were added to the reaction mixture, and the resulting $CF_3I$ was isolated by distillation.

EXAMPLE 4

10 g of powdered zinc were suspended in 100 ml dry dimethylformamide (DMF) and held at a temperature of approx. 30° C. Thereafter $CF_3Br$ was introduced into the liquid phase up to a maximum overpressure of approx. 1 bar (closed system) while being stirred very vigorously. The $CF_3Br$ dosing was regulated so that the reaction temperature did not exceed 40° C. After the reaction had ended, the pressure was relieved and the reaction mixture was freed of unreacted zinc by filtration. The solvent was removed under reduced pressure, while the distillation temperature was kept below approximately 50° C. to 60° C.

The resulting zinc compound of the formula $CF_3.Zn.Br.2DMF$ remained as a crystalline solid residue and may optionally be purified by washing with $CCl3F$ or toluene.

Analysis data:

Melting Point: 99°–100° C.

NMR data: d $(^{19}F) = -42.6$ ppm $(CF_3)$; d $(^{13}C) = 145.5$ ppm, quartet $(CF_3)$; $^1J$ $(^{19}F—^{13}C) = 358.3$ Hz; d $(^{13}C) = 165.8$ ppm $(C=O)$; d $(^{13}C) = 37.6$ ppm $(CH_3)$; d $(^{13}C) = 32.3$ ppm $(CH_3)$.

| Elemental analysis: $C_7H_{14}BrF_3N_2O_2Zn$ (360.49) | | | |
| --- | --- | --- | --- |
| | C | H | N |
| found (%) | 20.3 | 3.6 | 7.5 |
| calculated (%) | 23.3 | 3.9 | 7.8 |

EXAMPLE 5

30 g of the crystalline organo-zinc compound $CF_3.Zn.Br.2DMF$ were dissolved in 100 ml dried dimethylformamide under a protective gas atmosphere. Equimolar quantities of ICl were added to the solution, and the $CF_3I$ formed in the course of the reaction was isolated by distillation.

The $CF_3I$ produced in the Examples is free from impurities such as $CF_3H$ according to infrared spectroscopy and gas chromatography tests.

The foregoing description and examples have been set forth merely to illustrate and exemplify the invention and are not intended to be limiting. Since modifications of the described embodiments incorporating the spirit and substance of the invention may occur to persons skilled in the art, the scope of the invention should be construed in with reference to the appended claims and equivalents.

What is claimed is:

1. A method of producing $CF_3I$, comprising the steps of:
   (a) reacting in an unreactive solvent comprising at least one polar aprotic solvent selected from the group consisting of cyclic ethers, acyclic ethers, unsubstituted and substituted carboxylic acid amides, unsubstituted and substituted lactams, nitriles, sulfoxides, amines and pyridines, a compound corresponding to the formula $CF_3X$, wherein X represents Cl or Br, with a metal selected from the group consisting of magnesium, zinc, cadmium, bismuth and tin; and
   (b) reacting the resulting organometallic reaction product with a compound corresponding to the formula I-Y, wherein Y represents iodine or a ligand which is more electronegative than iodine, to produce $CF_3I$.

2. A method according to claim 1, wherein the reaction step (b) is carried out in a solvent selected from the group consisting of tetrahydrofuran, dioxane, diethyl ether, N,N-dimethylformamide, N,N-dimethylacetamide, N-methyl pyrrolidone, N-ethyl pyrrolidone, acetonitrile, benzonitrile, triethylamine, dimethyl sulfoxide, pyridine and methyl pyridine.

3. A method according to claim 1, wherein said metal is zinc.

4. A method according to claim 3, wherein step (a) further comprises isolating the resulting organometallic intermediate compound corresponding to the Formula (I)

$$CF_3.Zn.X.nL \qquad (I)$$

wherein X has the meaning given in claim 1, n represents the number 1 or 2 and L represents an organic, solar aprotic complexing agent.

5. A method according to claim 1 wherein said polar aprotic solvent is a ligand solvent selected from the group consisting of tetrahydrofuran, dioxane, diethyl ether, N, N-dimethylformamide, N, N-dimethylacetamide, N-methyl pyrolidone, N-ethyl pyrrolidone, acetonitrile, benzonitrile, triethylamine, dimethyl sulfoxide, pyridine and methyl pyridine.

6. A method according to claim 1, wherein the reaction in step (b) is carried out in a polar, aprotic solvent medium.

7. A method according to claim 4, wherein said complexing agent L is a ligand selected from the group consisting of cyclic ethers, acyclic ethers, unsubstituted and substituted carboxylic acid amides, unsubstituted and substituted lactams, nitriles, sulfoxides, amines and pyridines.

8. A method according to claim 4, wherein said solvent and said complexing agent are identical.

9. A method according to claim 8, wherein said solvent is an N-disubstituted carboxylic acid amide.

10. A method according to claim 9, wherein said N-disubstituted carboxylic acid amide is N,N-dimethylformamide (DMF).

11. A method according to claim 1, wherein step (a) is carried out in the presence of a catalytically effective quantity of a metal which is more electropositive than the metal used for the reaction.

12. A method according to claim 1, wherein step (a) is carried out in the presence of a Grignard reaction-activating additive.

13. A method according to claim 12, wherein said Grignard reaction-activating additive is a halogen-containing agent selected from the group consisting of iodine and $CCl_4$.

14. A method according to claim 1, wherein Y represents halogen.

15. A method according to claim 14, wherein said halogen is selected from the group consisting of chlorine, bromine and iodine.

16. A method according to claim 1, wherein step (a) is carried out at up to a maximum of 50 bar absolute pressure.

17. A method according to claim 16, wherein said pressure is in the range from 1 bar absolute up to the equilibrium pressure determined by the reaction temperature.

* * * * *